United States Patent
Grimard et al.

(10) Patent No.: US 10,338,036 B2
(45) Date of Patent: Jul. 2, 2019

(54) METHOD AND APPARATUS FOR SCANNING A TEST OBJECT AND CORRECTING FOR GAIN

(71) Applicant: TecScan Systems Inc., Boucherville (CA)

(72) Inventors: Nicolas Grimard, Montreal (CA); Rene Sicard, Brossard (CA); Sam H. Serhan, Brossard (CA)

(73) Assignee: TECSCAN SYSTEMS INC., Boucherville (CA)

(*) Notice: Subject to any disclaimer, the term of this patent is extended or adjusted under 35 U.S.C. 154(b) by 585 days.

(21) Appl. No.: 14/697,959

(22) Filed: Apr. 28, 2015

(65) Prior Publication Data
US 2015/0316513 A1 Nov. 5, 2015

Related U.S. Application Data

(60) Provisional application No. 61/987,195, filed on May 1, 2014.

(51) Int. Cl.
*G01N 29/44* (2006.01)
*G01N 29/04* (2006.01)
*G01N 29/26* (2006.01)
*G01N 29/30* (2006.01)

(52) U.S. Cl.
CPC ......... *G01N 29/4463* (2013.01); *G01N 29/04* (2013.01); *G01N 29/26* (2013.01); *G01N 29/30* (2013.01); *G01N 29/4427* (2013.01)

(58) Field of Classification Search
None
See application file for complete search history.

(56) References Cited

U.S. PATENT DOCUMENTS 3,608,361 A * 9/1971 Krautkramer ...... G01N 29/0609
 73/629
3,958,451 A * 5/1976 Richardson .......... G01N 29/223
 73/622

(Continued)

FOREIGN PATENT DOCUMENTS

| CA | 2820732 A1 | 12/2014 | |
| EP | 2007285 B1 | 2/2014 | |
| WO | WO 2014191661 A1 * | 12/2014 | ............. G01N 29/11 |

OTHER PUBLICATIONS

TecScan, Scan3D™: 3D Ultrasonic Scanner, Jun. 5, 2012.*
(Continued)

*Primary Examiner* — Justin Seo
*Assistant Examiner* — David L Singer
(74) *Attorney, Agent, or Firm* — BCF LLP (57) ABSTRACT

An apparatus for scanning a test object scans a reference object to build a gain correction map including gain values for scanning points on a surface of the reference object. The test object is also scanned to obtain measurements for scanning points on a surface of the test object. Amplitudes of the measurements obtained for the scanning points on the surface of the test object are normalized using the gain values of the gain correction map. The apparatus has a probe mounted on a mechanical scanner, and a controller controlling the scanning and normalizing operations. The apparatus can be used to create an image of the test object for non-destructive testing.

9 Claims, 5 Drawing Sheets

(56) References Cited

U.S. PATENT DOCUMENTS

| | | | | |
|---|---|---|---|---|
| 4,058,001 A * | 11/1977 | Waxman | A61B 8/00 348/163 |
| 4,389,893 A * | 6/1983 | Ophir | A61B 8/08 73/599 |
| 4,545,251 A * | 10/1985 | Uchida | G01N 29/0609 73/1.82 |
| 4,594,896 A * | 6/1986 | Cardoso | G01S 7/52025 73/599 |
| 4,660,419 A * | 4/1987 | Derkacs | G01N 29/30 250/252.1 |
| 5,119,678 A * | 6/1992 | Bashyam | G01B 17/02 73/602 |
| 5,257,624 A | 11/1993 | Fraser et al. | |
| 5,383,366 A * | 1/1995 | Wallingford | G01N 29/069 73/602 |
| 5,524,626 A * | 6/1996 | Liu | G01H 5/00 600/442 |
| 5,579,768 A | 12/1996 | Klesenski | |
| 5,644,512 A * | 7/1997 | Chernoff | G01Q 40/00 310/317 |
| 5,831,157 A * | 11/1998 | Woodmansee | G01N 29/0609 73/1.82 |
| 5,898,590 A * | 4/1999 | Wampler | G05B 19/401 33/504 |
| 5,940,123 A * | 8/1999 | Daigle | G01S 7/52044 348/163 |
| 6,120,446 A | 9/2000 | Ji et al. | |
| 6,364,835 B1 * | 4/2002 | Hossack | G01S 7/52034 600/443 |
| 6,487,910 B1 * | 12/2002 | Leybovich | G01N 29/11 73/600 |
| 7,343,019 B2 * | 3/2008 | Hankins | H03G 3/002 381/102 |
| 7,645,236 B2 | 1/2010 | Simopoulos et al. | |
| 7,833,159 B2 | 11/2010 | Ahn et al. | |
| 8,403,855 B2 | 3/2013 | Lee et al. | |
| 8,683,865 B2 | 4/2014 | Steinhoff et al. | |
| 2005/0150300 A1 * | 7/2005 | Nenno | G01N 29/0609 73/618 |
| 2006/0213250 A1 * | 9/2006 | Vaccaro | G01N 29/11 73/1.86 |
| 2007/0033991 A1 * | 2/2007 | Rice | B82Y 35/00 73/105 |
| 2007/0101815 A1 * | 5/2007 | Kollgaard | G01N 29/30 73/618 |
| 2008/0127733 A1 * | 6/2008 | Kurkcu | G01N 29/07 73/643 |
| 2008/0249405 A1 * | 10/2008 | Kakee | A61B 8/08 600/437 |
| 2009/0062648 A1 | 3/2009 | Derby, Jr. | |
| 2009/0069682 A1 * | 3/2009 | Hastings | G01S 7/52084 600/443 |
| 2009/0277269 A1 * | 11/2009 | Sarr | G01N 29/07 73/620 |
| 2010/0224000 A1 * | 9/2010 | Komatsu | G01N 29/04 73/602 |
| 2011/0270537 A1 * | 11/2011 | Wong | G01N 29/265 702/39 |
| 2012/0024067 A1 * | 2/2012 | Oberdoerfer | G01N 29/069 73/632 |
| 2012/0101764 A1 * | 4/2012 | McKeon | G01H 17/00 702/103 |
| 2012/0234073 A1 * | 9/2012 | Knorr | G01B 21/08 73/1.13 |
| 2012/0328176 A1 * | 12/2012 | Ren | A61B 6/025 382/132 |
| 2013/0340531 A1 * | 12/2013 | Hutchinson | G01N 29/11 73/633 |
| 2014/0024941 A1 * | 1/2014 | Umeda | A61B 8/14 600/445 |
| 2014/0238136 A1 * | 8/2014 | Ten Grotenhuis | G01N 29/0654 73/592 |
| 2014/0305217 A1 * | 10/2014 | Tapia | B64F 5/0045 73/618 |
| 2015/0000410 A1 * | 1/2015 | Grimard | G01N 29/265 73/634 |
| 2015/0035523 A1 * | 2/2015 | Lombardo | G01N 27/902 324/240 |
| 2016/0109283 A1 * | 4/2016 | Broussais-Colella | G01N 29/11 73/579 |

OTHER PUBLICATIONS

TecScan, Scan3D: Ultrasonic Immersion Tank, https://www.youtube.com/watch?v=SV9ZO2GC-U0, Published on Apr 12, 2012, 13 pages.*

TecScan, NDT Immersion Tank for Composite Fan Blades Testing, https://www.youtube.com/watch?v=XYVlod7LuH8, Published on Feb. 26, 2013, 10 pages.*

* cited by examiner

METHOD AND APPARATUS FOR SCANNING A TEST OBJECT AND CORRECTING FOR GAIN

TECHNICAL FIELD

The present disclosure relates to the field of non-destructive testing. More specifically, the present disclosure relates to a method and an apparatus for scanning a test object.

BACKGROUND

Mechanical scanning for ultrasonic inspection of regularly shaped objects, such as for example flat or slightly curved objects, is well documented and widely used. An object is typically mapped by software using a grid, for example a rectangular grid, in which a length and a width of each rectangular pixel of the grid is identical. The grid is typically aligned with main axes of a scanner, designated axes x and y, and a scanning motion is obtained by moving an ultrasonic probe along one axis or along a combination of axes (for instance x) and repeated after indexing along a perpendicular direction by moving one or a set of axes (for instance y), while maintaining a distance between the probe and the structure surface. Some systems use a plurality of such probes. An example of a method and apparatus for scanning an object is described in Patent Application No. CA 2,820,732, entitled "Method and Apparatus for Scanning an Object", to Grimard et al., filed on Jun. 27, 2013, the disclosure of which is incorporated by reference herein.

Trigger signals are generated to initiate ultrasonic pulse generation and data acquisition when the probe reaches positions set by the grid. Encoder signals of the main scanning axis (for example x) are monitored by an encoder counter that generates the trigger signals at required probe positions. The probe is indexed in a perpendicular direction by a distance dictated by dimensions of the pixels on the grid at the end of the scanning motion. The scanning motion is then repeated for a new index position.

The ultrasonic signal acquired at each position of the grid is amplified and filtered by a receiving apparatus using fixed filter and amplification settings. A selected time interval of this outputted signal is converted to digital data using an analog to digital converter apparatus. This digital data is recorded on a computer and the amplitude of the signal within a selected time interval (for instance the maximum absolute amplitude) or the time of occurrence of an echo within a selected time interval is associated to each position of the grid. An image named the C-scan is produced by associating colors of a chart to the values associated with each pixel of the grid.

Flaws are typically detected by analyzing the maximum amplitude of an ultrasonic signal within a selected time interval containing an ultrasonic echo that interacted with the test object. In the specific case of through transmission inspection, the echo that travelled from the emitting probe to the receiving probe and through the thickness of the tested object is monitored. Flaws are identified by comparison of the amplitude of one or a group of grid pixels with the amplitude of the surrounding pixels. An increase or decrease of signal amplitude exceeding a level obtained by calibration of the scanning apparatus on calibrated flaws, for example flat bottom holes, reveals the presence of a flaw.

The amplitude of an ultrasonic echo is a function of the presence of flaws, but also of variables associated with the object geometry and composition. Examples of variables that affect the amplitude of an ultrasonic echo interacting with an object are attenuation, diffraction, scattering, as well as changes of mechanical impedance. These variables can have various causes such as, for example, variations of thickness, surface curvature, material composition or the anisotropy of the material.

The amplifier gain of the receiver apparatus is set at a fixed value that allows monitoring the echo and the variations of amplitude of the echo in the presence of a flaw with an acceptable signal-to-noise ratio based on calibration.

For the example of a signal acquired by transmission of ultrasounds through a material, the amplifier gain must be set at a high enough level to monitor the expected variations of amplitude in the presence of a flaw, but low enough to avoid saturation of the echo by the receiver output limits or the acquisition input limits. In addition, the ratio of the signal amplitude recorded on a flawless area to the electronic noise level (i.e. the signal to noise ratio) must be higher than the expected signal amplitude loss due to a flaw.

Identification of flaws in objects of arbitrary shape, thickness and material composition is complicated by variations of echo amplitude naturally occurring within the tested material. If a sound material presents large differences in attenuation, the optimal receiver amplifier gain changes as a function of the attenuation. If the variation of attenuation between two areas of a sound object is too high, it can be impossible to set a unique receiver amplifier gain value that allows evaluating the condition of all areas of the object with the proper signal-to-noise ratio.

If the inspection of an object can be achieved with a fixed amplifier gain, data analysis must be performed with an a priori knowledge of the natural echo amplitude variations of the tested object in order to properly separate signal losses caused by flaws from natural signal amplitude variations.

Sizing of flaws is also complicated by variations of echo amplitude that are not related to flaw. Typical image flaw sizing methods such as −6 dB drop sizing or other C-scan based sizing that make use of echo amplitude require a constant amplitude reference to be reliable.

If the inspection of an object cannot be achieved with a fixed amplifier gain, current practice is to inspect different areas of the object individually at their optimal receiver gain or, when the geometry of the object allows it, to pause the scanning process and manually change the amplifier gain when the probe enters an area that required a different amplifier gain. In the case of an arbitrary object, both alternatives are impractical.

Therefore, there is a need for techniques that enable efficient scanning of test objects having complex geometries.

SUMMARY

According to the present disclosure, there is provided a method of scanning a test object. A reference object is scanned to build a gain correction map including a plurality of gain values for a corresponding plurality of scanning points on a surface of the reference object. The test object is also scanned to obtain a plurality of measurements for a corresponding plurality of scanning points on a surface of the test object. Amplitudes of the plurality of measurements obtained for the plurality of scanning points on the surface of the test object are normalized using the gain values of the gain correction map.

According to the present disclosure, there is also provided an apparatus for scanning a test object. The apparatus comprises a mechanical scanner, a probe and a controller. The probe is mounted on the mechanical scanner. The controller is operably connected to the mechanical scanner and to the probe. The controller controls a scanning motion of the probe to obtain a plurality of measurements for a corresponding plurality of scanning points on a surface of a reference object, builds a gain correction map including a plurality of gain values calculated as a function of the plurality of scanning points on the surface of a reference object, controls a scanning motion of the probe to obtain a plurality of measurements for a corresponding plurality of scanning points on a surface of the test object, and normalizes amplitudes of the plurality of measurements obtained for the plurality of scanning points on the surface of the test object using the gain values of the gain correction map.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various drawings.

DETAILED DESCRIPTION

Various aspects of the present disclosure generally address one or more of the problems of scanning test objects having complex geometries.

The following terminology is used throughout the present disclosure:

Test object: any object for which it is desired to obtain a physical analysis.

Reference object: an object similar in geometry to the test object; as an example, the test object and the reference object may be similar items, the test object having potential flaws due to wear and tear, the reference object being new.

Scanning point: one of a plurality of points on the surface of an object where a scanning measurement is obtained.

Gain value: a value representative of a level of attenuation of a scanning signal at a given scanning point of an object.

Gain correction map: a list of gain values for a number of scanning points of the reference object.

Normalization: adjustment of a measured value using a corresponding gain value.

Pulse: a brief signal emitted by a probe.

Pulse-echo mode: signal acquisition mode of a probe in which a pulse is emitted by the probe and a reflected signal is acquired by the same probe.

Transmission mode: signal acquisition mode in which a pulse is emitted by an emitting probe and acquired by a receiving probe after transmission through an object.

Probe: a physical device capable of sending and/or receiving a signal towards an object being scanned.

Mechanical scanner: a mechanical device capable of moving under control of a controller while supporting a probe.

Controller: a processor, a computer, a combination of processors and/or computers, possibly including a memory, an interface, and similar components, the controller may be hardwired for carrying a function or may comprise programmable code for carrying a function.

Non-transient memory: a memory device that maintains stored information in the absence of electrical power.

Command: a control signal sent from a first component to a second component for initiating an action of the second component.

Non-destructive testing: a material evaluation technique that does not cause damage to an object under test.

C-scan image: an image constructed based on information from signals resulting from scanning of an object, the signals being obtained at a plurality of scanning points on the surface of the object.

In an embodiment, the present disclosure presents a method of scanning a test object. In another embodiment, the present disclosure presents an apparatus for scanning a test object. The disclosed method and apparatus can be used for various applications, including without limitation for non-destructive testing purposes.

Figure 1:
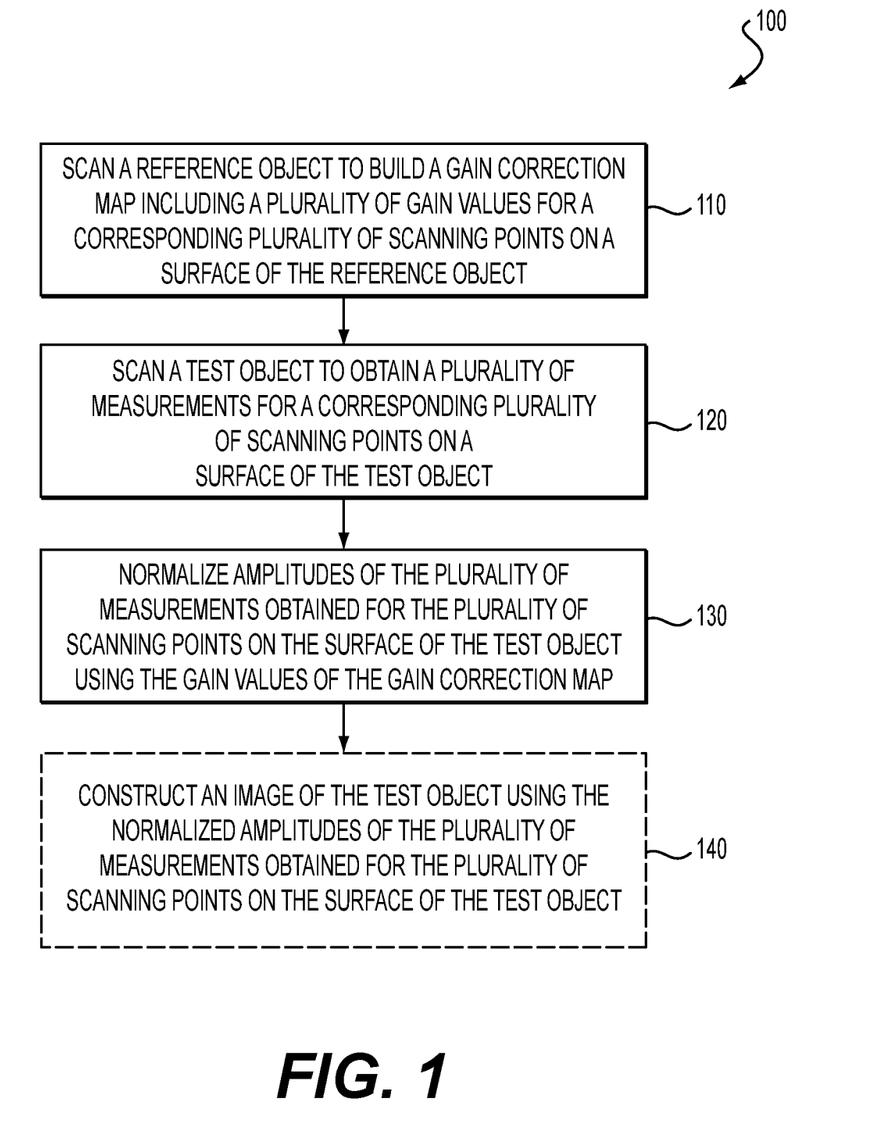
FIG. 1 is a flowchart showing operations of a method for scanning a test object.

Referring now to the drawings, FIG. 1 is a flowchart showing operations of a method for scanning a test object. In FIG. 1, a sequence 100 comprises a plurality of operations that may be executed in variable order, some of the operations possibly being executed concurrently, some of the operations being optional. Operation 110 comprises scanning a reference object, similar in geometry to the test object, to build a gain correction map including a plurality of gain values for a corresponding plurality of scanning points on a surface of the reference object. The scanning points on the surface of the reference object may be defined on a rectangular grid. The gain values for the plurality of scanning points on the surface of the reference object may be stored in a non-transient memory. In order to minimize possible noise effects or localized effects that may not be reproducible amongst similar objects, the gain values may be filtered or smoothed prior to their use or storage.

The test object is also scanned at operation 120 to obtain a plurality of measurements for a corresponding plurality of scanning points on a surface of the test object. There is at least some correspondence between the scanning points on respective surfaces of the reference object and of the test object. In a first variant of the method, scanning paths on the surfaces of both objects may be identical and there may be a one to one correspondence between scanning points on surfaces of the reference object and of the test object. In a second variant of the method, the scanning points may follow similar scanning paths on the surfaces of both objects, possibly following similar rectangular grids or any other similar grids. The gain values of the gain correction map may be interpolated if a number of scanning points on the surface of the reference object is not equal to a number of scanning points on the surface of the test object.

Scanning the reference object and the test object may be executed using ultrasonic pulses applied at each scanning point of the surfaces of the reference object and of the test object. The scanning may involve detecting amplitudes of signals resulting from pulse-echo or transmission of the ultrasonic pulses on each of the scanning points on the surfaces of the reference object and of the test object. Amplitudes of the plurality of measurements obtained for the plurality of scanning points on the surface of the test object are normalized at operation 130, using the gain values of the gain correction map. An image of the test object may be constructed at operation 140, using the normalized amplitudes of the plurality of measurements obtained for the plurality of scanning points on the surface of the test object.

In the same or other variants of the method, when detecting the amplitudes of the signals resulting from pulse-echo or transmission of the ultrasonic pulses on each of the scanning points on the surfaces of the reference object and of the test object, a maximum of each amplitude signal over a predetermined time interval is determined. A reference amplitude for the reference object may be determined by selecting a maximum value among the amplitudes of the signals resulting from pulse-echo or transmission of the ultrasonic pulses on each of the scanning points on the surface of the reference object. The gain values for the plurality of scanning points on the surface of the reference object may then be set as a function of corresponding amplitudes of the signals resulting from pulse-echo or transmission of the ultrasonic pulses on each of the scanning points on the surface of the reference object in relation to the reference amplitude, for example by calculation ratios of corresponding amplitudes of the signals resulting from pulse-echo or transmission of the ultrasonic pulses on each of the scanning points on the surface of the reference object and of the reference amplitude.

To normalize the amplitudes of the signals resulting from pulse-echo or transmission of the ultrasonic pulses on each of the scanning points on the surface of the test object, they may be amplified using gain values calculated as a function of the amplitudes of the signals resulting from pulse-echo or transmission of the ultrasonic pulses on each of the scanning points on the surface of the reference object.

When the reference object is symmetrical along an axis, execution time of the sequence 100 may be reduced by scanning the reference object over a part of its surface on one side of the axis. Gain values determined for a corresponding plurality of scanning points on the one side of the axis are then replicated on corresponding unscanned points on another side of the axis.

Figure 2:
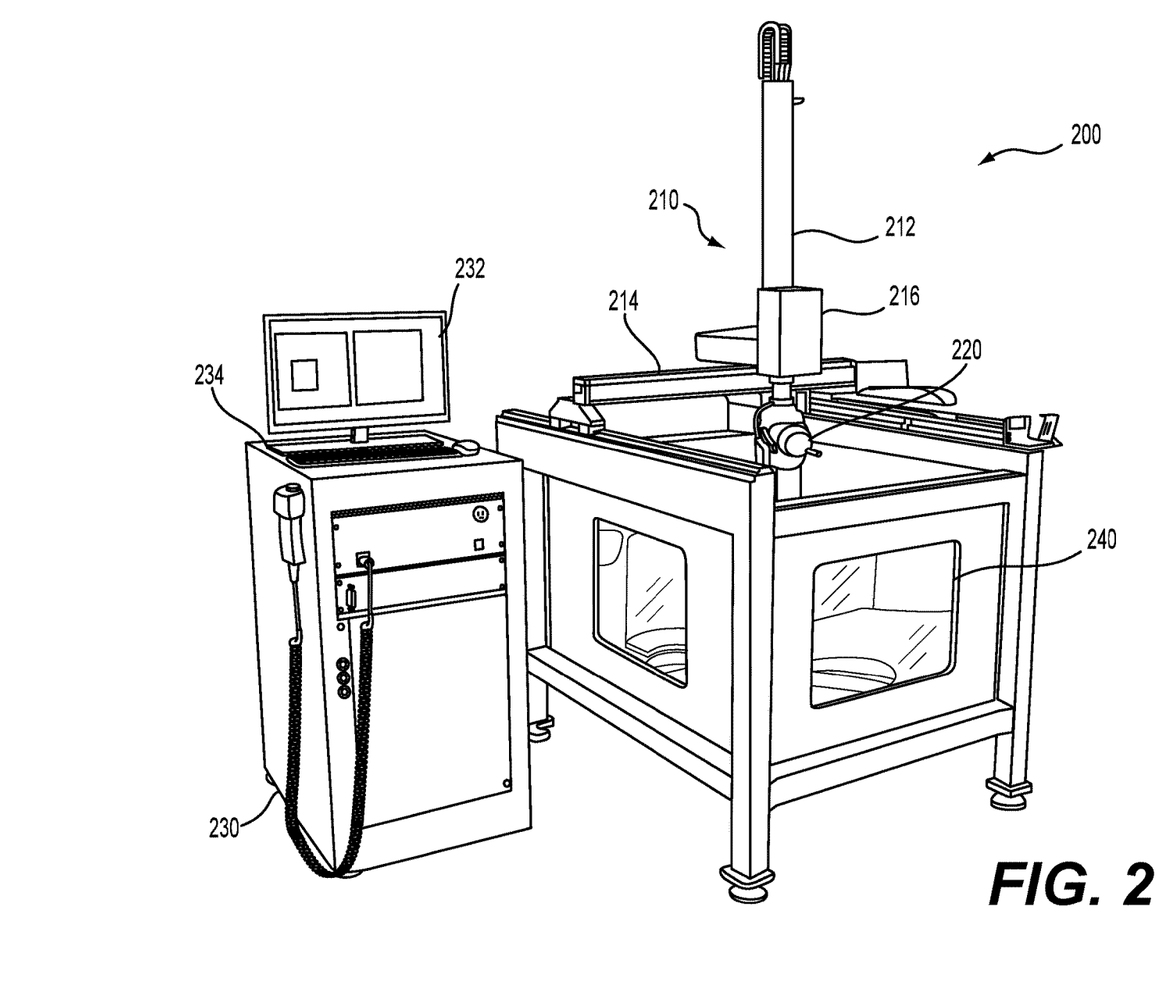
FIG. 2 is a perspective view of an apparatus for scanning a test object according to an embodiment.

FIG. 2 is a perspective view of an apparatus for scanning a test object according to an embodiment. An apparatus 200 as illustrated is one of many possible realizations of a scanning apparatus capable of executing the operations of the above described sequence 100. Some of the shown components of the apparatus 200 are optional and may not be present in some embodiments.

The apparatus 200 comprises a mechanical scanner 210, a probe 220 mounted on the mechanical scanner 210, and a controller 230. As illustrated, the probe 220 is held within a basin 240 that may be filled with a couplant material, for example water, air, or another fluid, the couplant material forming a controlled environment for transmission of probe signals. The mechanical scanner 210 as shown is capable of moving the probe 220 along three (3) axes by raising or lowering a vertical member 212, moving the vertical member 212 laterally along a length of an horizontal beam 214, and by moving the horizontal beam 214 longitudinally along a length of the basin 240. The vertical member 212 and the horizontal beam 214 are moved by a motion controller 216, which itself receives commands from the controller 230. The apparatus 200 can thus scan an object over a three-dimensional (3D) space. The mechanical scanner 210 and the probe 220 are connected by wires (not shown) to the controller 230; they may be connected wirelessly to the controller 230 in other variants. The controller 230 includes a screen 232 and a keyboard 234 allowing an operator to control the apparatus 200 and its components.

The controller 230 controls a scanning motion of the probe 220 to obtain a plurality of measurements for a corresponding plurality of scanning points on a surface of the reference object. It builds a gain correction map including a plurality of gain values calculated as a function of the plurality of scanning points on the surface of a reference object. The controller 230 also controls a scanning motion of the probe 220 to obtain a plurality of measurements for a corresponding plurality of scanning points on a surface of the test object. Finally, the controller 230 normalizes amplitudes of the plurality of measurements obtained for the plurality of scanning points on the surface of the test object using the gain values of the gain correction map.

The apparatus 200 may comprise a memory (not shown) in which the controller 230 stores and reads the correction gain map. An image generator constructs an image, for example a C-scan image, of the test object using the normalized amplitudes of the plurality of measurements obtained for the plurality of scanning points on the surface of the test object. A visual display such as the screen 232 may show the image. Alternatively, the image may be printed on a printer (not shown) or an output port (not shown) of the controller 230 may transmit data representing the image.

Figure 3:
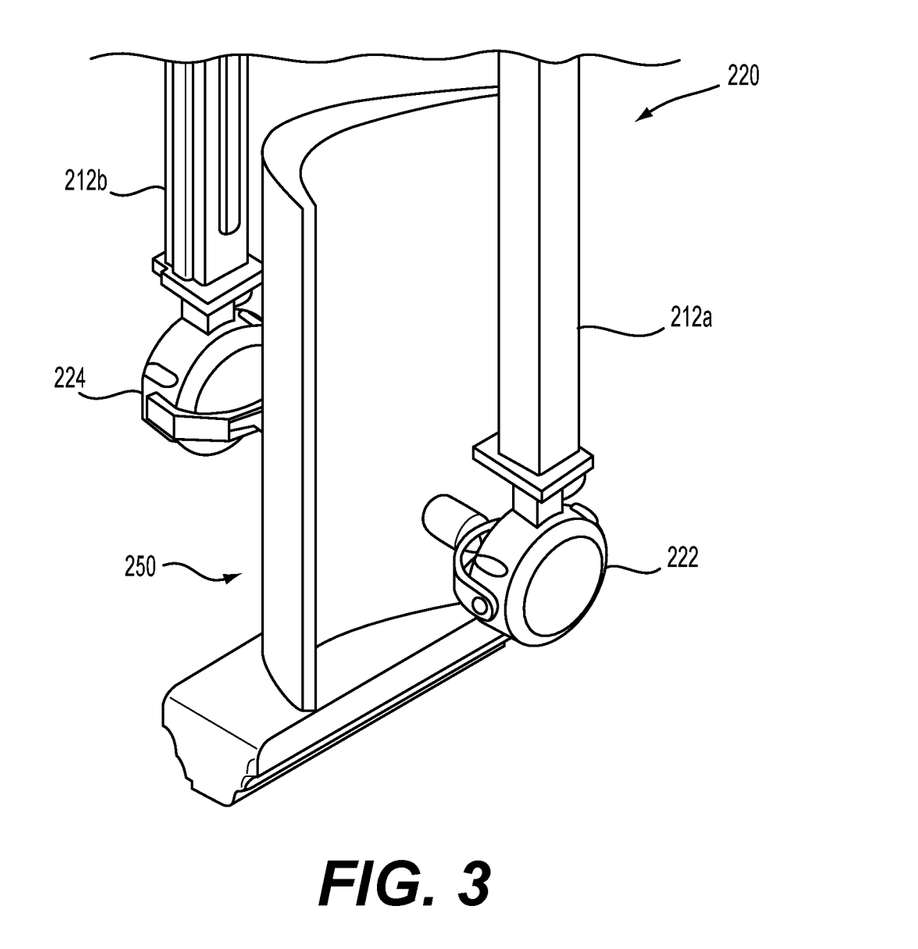
FIG. 3 is a detailed view of an example of emitting and receiving ultrasonic probes operating in transmission mode.

FIG. 3 is a detailed view of an example of emitting and receiving ultrasonic probes operating in transmission mode. The probe 220 of FIG. 2 includes an emitting probe 222 and a receiving probe 224, both of which operate in ultrasonic mode in the non-limiting example of FIG. 3. The vertical member 222 of FIG. 2 doubles at its lower end into members 212a and 212b for respectively mounting the emitting probe 222 and the receiving probe 224. An object 250, which may be a reference object or a test object, is held between the emitting probe 222 and the receiving probe 224. While FIG. 3 shows an example of emitting and receiving ultrasonic probes operating in transmission mode, other types of probes such as air coupled probes, eddy current probes, laser probes, hybrid probes, and the like, operating in transmission mode or in pulse-echo mode, are also contemplated. Also, while FIG. 3 shows one (1) pair of emitting and receiving probes 222 and 224, use of multi-element probes and use of phased arrays or probes, operating in pulse-echo mode or in transmission mode, are also contemplated.

Figure 4:
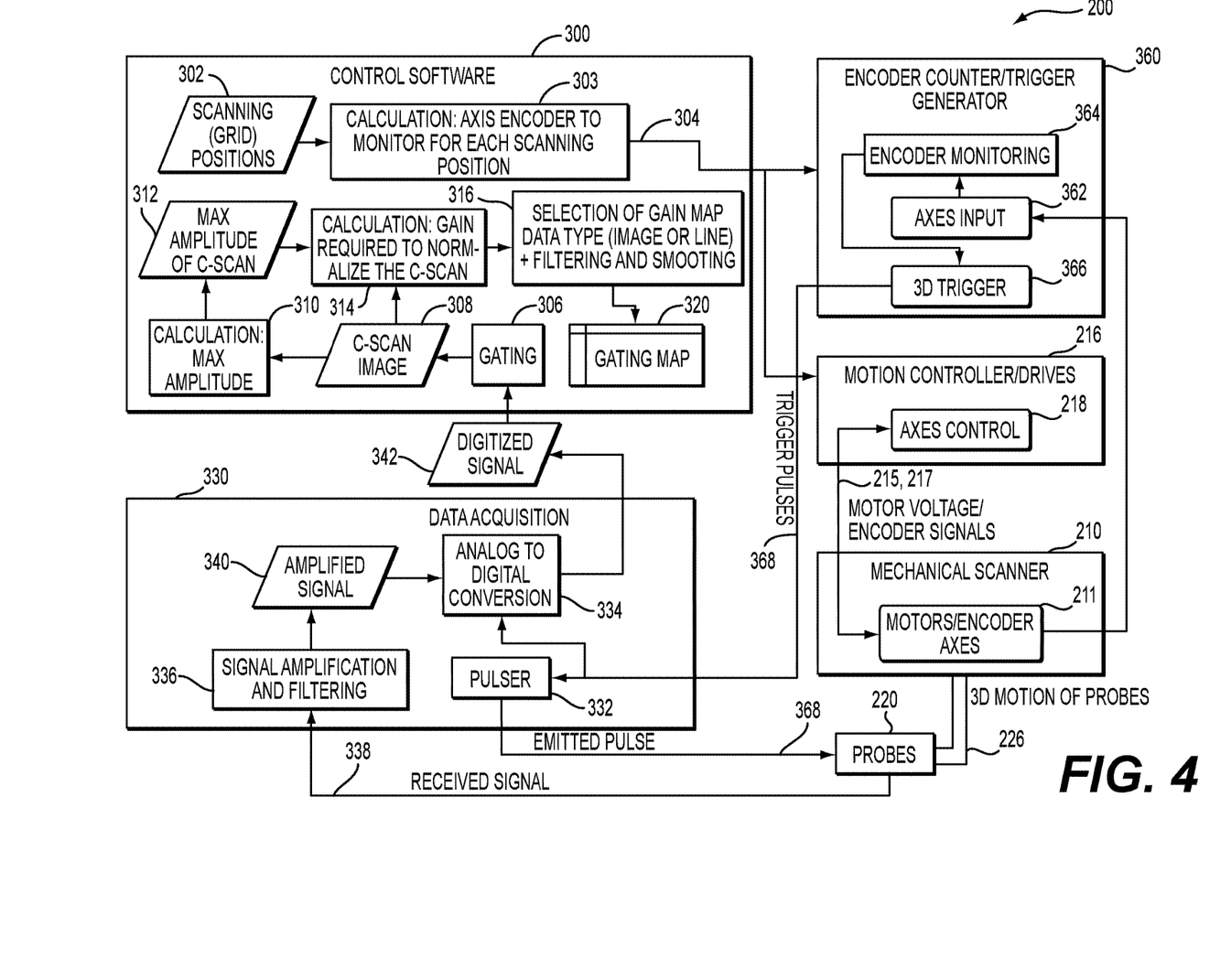
FIG. 4 is a block diagram of the scanning apparatus of FIG. 2 showing an information flow within the apparatus when building a gain correction map.
Figure 5:
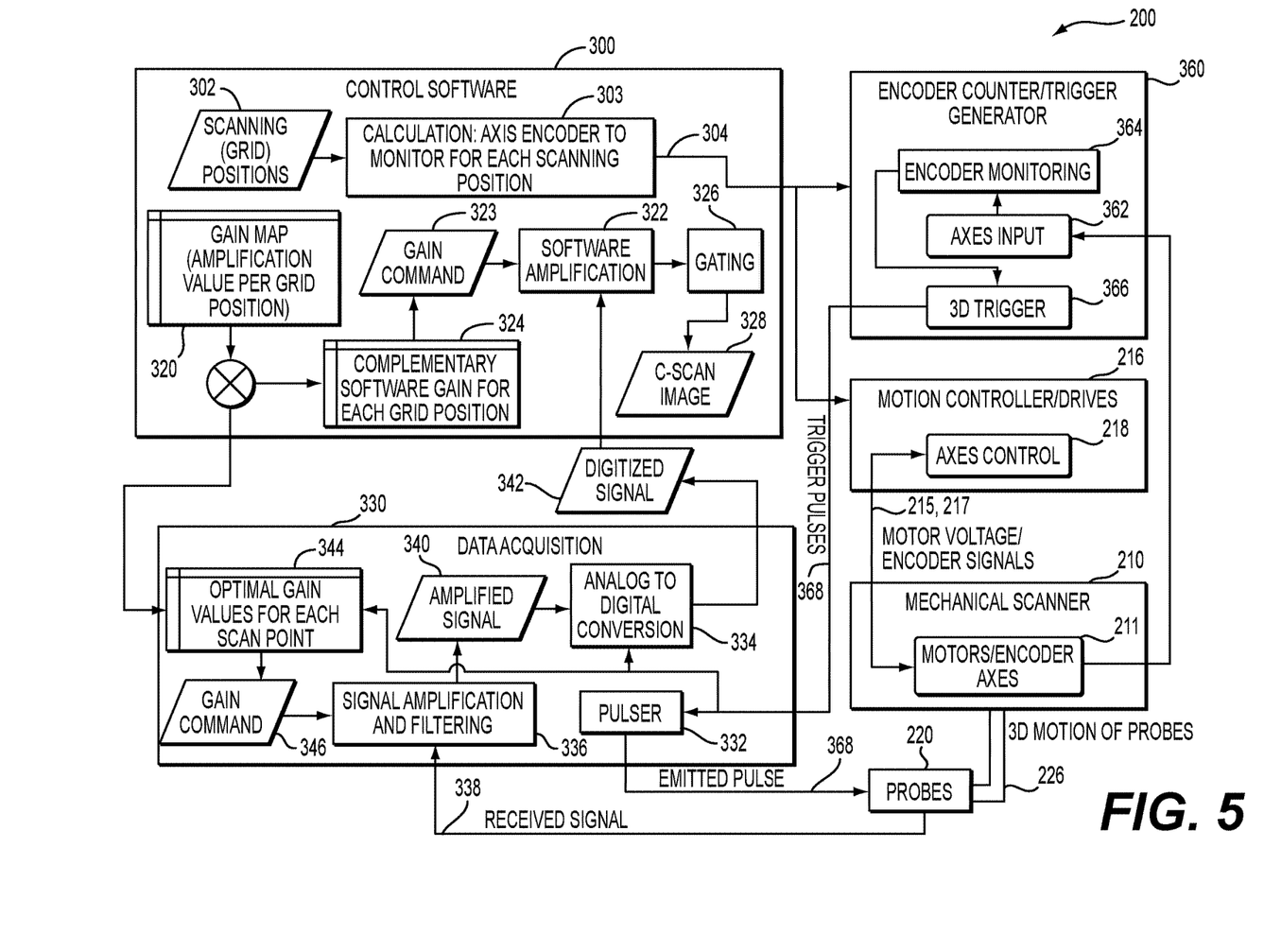
FIG. 5 is a block diagram of the scanning apparatus of FIG. 2 showing an information flow within the apparatus when scanning a test object.

FIG. 4 is a block diagram of the scanning apparatus of FIG. 2 showing an information flow within the apparatus when building a gain correction map. FIG. 5 is a block diagram of the scanning apparatus of FIG. 2 showing an information flow within the apparatus when scanning a test object. FIGS. 4 and 5 depict the same apparatus 200 and only differ in the manner in which they show their information flows. For illustration purposes, FIGS. 4 and 5 are described in the context of the apparatus 200 having a 3D mechanical scanner 210.

Referring at once to FIGS. 4 and 5, the apparatus 200 comprises the mechanical scanner 210 having the motion controller 216 and one or more probes 220. A control software module 300, a data acquisition unit 330 and an encoder counter/trigger generator 360 are interconnected to the mechanical scanner 210 and to the probes 220. The control software module 300, the data acquisition unit 330 and the encoder monitoring module 360 may in whole or in part be integrated in the controller 230 of FIG. 2.

Features of the apparatus 200 common to both FIGS. 4 and 5 will first be described. Based on a predefined scanning path 302, for example a rectangular grid, defined according to the geometries of the reference object and test object, the control software module 300 includes a probe position information calculator 304 that calculates axis encoder positions 304 (i.e. three (3) positions over 3D for each scanning point) for each subsequent scanning point on the scanning path 302. The control software module 300 provides each subsequent axis encoder positions 304 to the encoder counter/trigger generator 350 and to the motion controller 216.

The mechanical scanner 210 includes three (3) motors and axis encoders 211 that detect movements 226 of the probe 220 over 3D and provide probe position information 215 to axis controllers 218 of the motion controller 216. The axis controllers 218 use the axis encoder positions 304 and the probe position information 215 to provide positioning commands 217 to the mechanical scanner 210 to move the probes 220 while minimizing differences between the desired axis encoder positions 304 and the actual probe position information 215.

The mechanical scanner 210 also provides the probe position information 215 to an axis input port 362 of the encoder counter/trigger generator 360. An encoder monitoring process 364 analyses the desired axis encoder positions 304 and the actual probe position information 215 and causes a 3D trigger module 366 to generate pulse commands 368 when the probes 220 are at the desired position.

In the data acquisition unit 330, a pulser 332 receives the pulse commands 368 and forwards them to the probes 220. The pulse commands 368 are also applied to an analog to digital converter 334. A signal amplification and filtering module 336 (that at the time does not use any gain signal) receives response signals 338 from the probes 220. Amplified signals 340 are also fed to the analog to digital converter 334 digitized versions 342 of the pulse commands 368 and of the response signals 338 are sent to the control software module 300.

When building the gain correction map, the reference object is being scanned by the apparatus 200. As shown on FIG. 4, the digitized versions 342 of the pulse commands 368 and of the response signals 338 are gated 306 to extract peak values of the response signals 338. An image generator 308 produces a C-scan image of the reference object. A calculator 310 detects a maximum amplitude 312 among the peaks of the C-scan image. A normalizer 314 evaluates gains required to normalize the C-scan image, optionally computing the gain values as a function of the maximum amplitude 312, for example as a ratio of each peak value over the maximum amplitude 312. A selector 316 chooses a gain map data type, in which gain values are determined in terms of image or line values. The selector 316 optionally filters and/or smoothes the gain values. The resulting gain values are stored in a memory (not specifically shown) as a gain correction map 320. The gain correction map 320 contains gain values (i.e. amplification values) for each scanning position of the scanning path 302.

When the test object is being scanned by the apparatus 200, as shown on FIG. 5, the gain correction map 320 for a reference object having sharing a similar geometry with the test object is loaded. Gain values from the gain correction map 320 are used both in the control software 300 and in the data acquisition unit 330.

In the data acquisition unit 330, the gain correction map 320 provides gain values 344 for each scanning point. The pulse commands 368 are used as triggers for reading the gain value 344 relevant to a given point being scanned. The gain value 344 is used to generate a gain command 346 that is applied to the signal amplification and filtering module 336. As such, the response signal 338 is normalized at least in part using the gain command 346 before being submitted to the analog to digital converter 334. The digitized versions 342 of the pulse commands 368 and of the amplified response signals 338 are fed to a software amplification module 322. The software amplification module 322 applies to the digitized signal 342 a gain command 323 calculated based on a complementary software gain 324 obtained by selecting a gain value for the appropriate scanning point from the gain correction map 320, producing further amplified and normalized outputs. Outputs of the software amplification module 322 are gated 326 to extract peak values of these outputs. An image generator 328 collects the outputs of the gate 326 to form a normalized C-scan image of the test object.

Various embodiments of the method and apparatus for scanning a test object, as disclosed herein, may be envisioned. One such embodiment may comprise a scan gain mapping method dedicated to ultrasonic inspection of complex materials such as aerospace composite parts of arbitrary shape, thickness and material composition.

The method provides a normalized ultrasonic inspection output of a test sample of arbitrary geometry and/or having varying material composition. The amplitude of an ultrasonic echo signal is a function of the presence of flaws, but also of variables associated with the object geometry and composition. Examples of variables of an object that affect the amplitude of an ultrasonic echo are attenuation, diffraction, scattering, reflection coefficient, transmission coefficient. These variables can have various causes such as, for example, variations of thickness, variations of surface curvature, variation of material composition or the anisotropy of the material.

An inspection is performed by moving one or multiple probes along the surface of the test object on a rectangular grid pattern within a given orthogonal space (Euclidian, cylindrical, polar or generalized parametric space for complex surfaces). Ultrasonic waves are emitted, received, amplified filtered and stored each time the probe reaches the positions set by the grid. A C-scan image is typically built by monitoring the amplitude of an echo within a given time frame (gate). It could also represent the time-of-flight of an echo, its equivalent thickness inside a material or any other amplitude/time feature observable on the ultrasonic signal.

Conventional practice has been to set the amplifier gain of the receiver at a value that allows seeing the echo of a flawless area below the saturation limit of the ultrasonic apparatus (receiver and acquisition card) and with an amplitude that is high enough to detect variations of echo amplitude at a level established using a reference sample.

In the specific case of through transmission inspection (ultrasonic waves propagating from an emitting probe, through the thickness of the object and to a receiving probe on the other side of the object), a flaw is identified by an attenuation of the transmitted signal, i.e. a drop of its amplitude relative to an adjacent flawless area. This is typically detected by the use of an amplitude threshold gate which level is set as a given drop referred to the amplitude of a flawless signal. A minimum signal-to-noise ratio is therefore required in order to identify a signal drop corresponding to a flaw. Considering the example of a signal acquired by transmission of ultrasounds through a material, the signal amplification (receiver gain) is set at a level that limits the signal amplitude within the range of the acquisition instrument, while being high enough to monitor variations of amplitude caused by the presence of a flaw. If a single amplification level is used for all areas of the object (common practice), the detection of flaws can be compromised; in areas where natural signal loss is high, it becomes impossible to identify a flaw if the electronic noise level is higher than the amplitude that is expected in the presence of a flaw. Furthermore, if the echo amplitude of the flawless areas vary too much during the inspection of the object, it becomes impossible to set a unique amplitude detection threshold gate since the reference from which the threshold is established changes as a function of probes position. Thus flaws can be missed.

The disclosed method normalizes the ultrasonic response of the object in order to minimize or remove the amplitude variations that are not related to flaws, i.e. solely due to material properties and geometry, as well as reproducible mechanical imprecisions of the scanning apparatus. It makes use of the positional reproducibility of an automated scanner combined with a reference, flawless object to create a map of the differences in ultrasonic signal amplitude caused by attenuation along the test object. This map is then used in conjunction with the gain control of the amplifier of the ultrasonic receiver to normalize the ultrasonic response when scanning a comparable object. With such a normalized response, flaws can be identified more easily by threshold gating.

Objects with arbitrary geometries are inspected by a computer controlled motion control system adjusting the position and orientation of an ultrasonic test probe (or a plurality of probes) so that it follows the surface of the arbitrary object at a constant distance. The orientation of the probe is adjusted to compensate for surface curvature and refraction effects. At each sampling point on the test specimen, a trigger signal is sent to a computer controlled pulser-receiver which sends an ultrasonic pulse and receives and amplifies the transmitted and/or reflected echoes. A waveform digitizer is then used to transfer the amplified signal to the computer. The echo amplitudes of the sampling points are organized into the C-scan image.

Variations in local thickness and material composition of arbitrary objects produce variations in the ultrasonic echo amplitude acquired at different locations on the object. Furthermore, mechanical imprecisions also contribute to variations in the echo amplitudes over the part. Without normalization, the resulting variation in the C-scan image amplitudes would decrease the reliability of flaw detection and sizing.

Normalization through scan gain mapping corrects such variations, effectively generating a uniform ultrasonic echo amplitude on all the sample points. At a first operation of the process, a reference sample containing no flaws is inspected. The resulting amplitude C-scan image is processed to determine, for each point, the gain adjustment required to obtain a uniform amplitude response over the entire C-scan image. This gain adjustment matrix is called the scan gain map. For bidirectional scanning applications, two different gain matrices are produced, one for the positive direction scan lines and the other for the negative direction scan lines, which are typically different due to mechanical backlash. Filtering or B-Spline surface fitting can be applied to the gain adjustment matrices in order to eliminate the effects of structural noise that are not reproducible from one sample to another.

Once the gain matrices are obtained from the reference sample, tests samples having the same geometry can be inspected. Before performing the scan, a gain control sequence is constructed from the gain matrices and sent to the computer controlled pulser-receiver unit. Using this gain control sequence and the sampling point trigger signal, the pulser-receiver unit automatically changes the signal gain for each sampling point on the test sample. The resulting C-scan, in the absence of flaws, will have a constant amplitude throughout the whole grid, thus allowing for more reliable flaw detection and sizing.

This method is particularly well suited for through-transmission scanning, where loss of amplitude is typically monitored to detect the presence of flaws. It is common for samples of complex shapes to present thickness variations that result in natural signal amplitude loss in thick areas that is comparable to a signal amplitude loss associated to flaws in thinner sections. Using scan gain mapping normalizes the amplitude of the transmitted echoes, compensating for natural sources of amplitude variations. This results in ultrasonic signals for which amplitude losses are solely due to the presence of flaws. This improves the capabilities of performing measurements such as sizing and signal-to-noise ratio of flaws.

The process is separated in two operations: 1) Construction of a gain correction map for the object using a reference object; 2) Application of the gain correction map during an inspection to normalize the response of the object to the response of the reference object.

Here, scanning and indexing lines represent consecutive grid pixels along the axes of the width and length of the rectangular grid arrangement. The scanning line is aligned along the physical or virtual axis that moves continuously along the object, while the indexing line is aligned with the other physical or virtual axis that indexes the probe from one scan line to the other during the scan.

A mechanical scanner comprising a combination of linear and/or angular axes of motion is used to move one or multiple probe(s) along the surface of an object. Each axis is moved by a motor and the position of the axis is given by a positional encoder device. A motion controller is used in combination with amplifier drives to control the motors.

The surface of the object is mapped using a rectangular grid where each element of the grid represents a position where ultrasonic waves are generated and received by the ultrasonic probe, and where signal acquisition is done.

For each grid position, the control software determines the optimal axis encoder to be monitored in order to know when the scanner reaches the grid position. A trigger pulse signal is generated when the axis is at the grid position. The trigger signal is received by the ultrasonic pulser to generate an electrical impulse that is sent to the emitting probe(s). The trigger signal is also received by the analog-to-digital converter to synchronize the waveform acquisition with the emitted electrical impulse.

The ultrasonic probe converts the electrical impulse into an ultrasonic wave. The ultrasonic wave interacts with the object, and then travels to the receiving probe which converts it to an electrical signal. The receiving probe can be the same probe as the one that generated the ultrasonic signal or a different probe.

The electrical signal generated by the receiving probe(s) inputs the receiver and is filtered and amplified by the receiver. The amplification is set to avoid any saturation of the signal after amplification.

The amplified analog signal is then converted to a digital signal by an analog-to-digital converter (digitizer).

The digitized signal is transferred to the computer and a gate is used to extract an amplitude from the signal within a time interval set by the gate. This amplitude value is typically but not restricted to the peak amplitude of the signal within the gate. Alternatively, the gate could be applied on the analog signal and the resulting amplitude data could be digitized and transferred to the computer.

The amplitude value obtained by the gate is then stored and associated to the current point of the grid. A C-scan image consisting of all the amplitude values placed within a rectangular grid corresponding to the scanned grid is created.

The maximum amplitude of the C-scan image is found and used as the reference amplitude. The amplification required to increase the amplitude of all other positions of the grid to match the maximum amplitude of the C-scan is calculated.

A new data set utilizing the same grid is obtained, where each item of the grid contains the amplification calculated in the previous operation. The gain map is the result of this operation.

Alternatively, if the object is symmetrical along one axis of the scanned grid, for instance the scanning axis, the gain map can be obtained by selecting a representative row of pixels of the grid along the other axis, i.e. the indexing axis, and by filling the gain map grid by reproducing this row of pixels along the scanning axis.

Filtering and smoothing algorithms can also be applied on the gain map to minimize the effects of noise or localized effects that may not be reproducible amongst identical objects.

A mechanical scanner comprising a combination of linear and/or angular axes of motion is used to move one or multiple probes along the surface of an object. Each axis is moved by a motor and the position of the axis is given by a positional encoder device. A motion controller is used in combination with amplifier drives to control the motors.

The surface of the object is mapped using a rectangular grid where each element of the grid represents a position where ultrasonic waves are generated and received by the ultrasonic probes.

A gain map corresponding to the object and the grid is recalled from the computer memory. If the number of elements of the grid is not the same as the number of elements of the gain map, the content of the latter is sampled or interpolated to match the grid size. For each element of the grid, the maximum control gain value that is below the required gain defined in the gain map is stored in the internal memory of the ultrasonic unit. Since the ultrasonic unit gain can only be controlled by discrete values, the difference between the gain map value and the control gain calculated for each element of the grid is stored as a complementary software gain data on the computer.

For each grid position of the scanning line, the control software determines the optimal axis encoder to be monitored in order to know when the scanner reaches the grid position. A trigger pulse signal is generated when the axis is at the grid position. The trigger signal is received by the ultrasonic pulser to generate an electrical impulse that is sent to the emitting probe(s). The trigger signal is also received by the analog-to-digital converter to synchronize the waveform acquisition with the emitted electrical impulse. The ultrasonic unit also uses the trigger signal to select the gain control command associated with the current element of the grid.

The ultrasonic probe(s) converts the electrical impulse into an ultrasonic wave. The ultrasonic wave interacts with the object and is converted to an electrical signal by the receiving probe(s). The receiving probe(s) can be the same probe(s) as the one that generated the ultrasonic signal or a different probe(s).

The electrical signal generated by the receiving probe(s) signal inputs the receiver and is filtered and amplified by the receiver at the amplification level corresponding to the gain command selected at the reception of the trigger signal.

The amplified analog signal is then converted to a digital signal by an analog-to-digital converter (digitizer).

The digitized signal is transferred to the computer. The complementary software gain value of the current grid position is then applied on the digital signal by mean of software amplification.

A gate is used to extract an amplitude from the signal within a time interval set by the gate.

This amplitude value is typically but not restricted to the peak amplitude of the signal within the gate. The amplitude value obtained by the gate is then stored and associated to the current point of the grid. A C-scan image consisting of all the amplitude values corresponding to the rectangular grid and having the same dimensions as the grid is created.

Those of ordinary skill in the art will realize that the description of the method and apparatus for scanning a test object are illustrative only and are not intended to be in any way limiting. Other embodiments will readily suggest themselves to such persons with ordinary skill in the art having the benefit of the present disclosure. Furthermore, the disclosed method and apparatus may be customized to offer valuable solutions to existing needs and problems of scanning test objects having complex geometries.

In the interest of clarity, not all of the routine features of the implementations of the method and apparatus are shown and described. It will, of course, be appreciated that in the development of any such actual implementation of the method and apparatus, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of non-destructive testing having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. An apparatus for scanning a test object, comprising:
a mechanical scanner;
a probe mounted on the mechanical scanner; and
a controller operably connected to the mechanical scanner and to the probe, the controller being configured to:
control a bidirectional scanning motion of the probe to obtain a first plurality of measurements for a first corresponding plurality of scanning points defined over a positive direction scan line on a surface of a reference object and to obtain a second plurality of measurements for a second corresponding plurality of scanning points defined over a negative direction scan line on the surface of the reference object;
build a first gain correction map including a first plurality of gain values calculated as a function of the first plurality of scanning points on the surface of the reference object;
build a second gain correction map including a second plurality of gain values calculated as a function of the second plurality of scanning points on the surface of the reference object;
control a bidirectional scanning motion of the probe to obtain a third plurality of measurements for a third corresponding plurality of scanning points defined over a positive direction scan line on a surface of the test object and to obtain a fourth plurality of measurements for a fourth corresponding plurality of scanning points defined over a negative direction scan line on the surface of the test object; and
normalize amplitudes of the third and fourth pluralities of measurements obtained for the third and fourth pluralities of scanning points on the surface of the test object using the gain values of the first and second gain correction maps.

2. The apparatus of claim 1, comprising:
an image generator configured to construct an image of the test object using the normalized amplitudes of the third and fourth pluralities of measurements obtained for the third and fourth pluralities of scanning points on the surface of the test object; and
a visual display for showing the image.

3. The apparatus of claim 1, wherein the probe comprises one or more ultrasonic probes.

4. The apparatus of claim 1, wherein the probe comprises an emitting probe and a receiving probe, the receiving probe being configured to detect a transmitted or reflected signal resulting from a signal of the emitting probe.

5. The apparatus of claim 1, wherein the controller comprises:
a probe position information calculator providing positioning commands to the mechanical scanner based on position information calculated in view of the first and second pluralities of scanning points on the surface of the reference object and on the third and fourth pluralities of scanning points on the surface of the test object;
an encoder monitoring module receiving the calculated position information from the probe position information calculator, receiving actual probe position information from the mechanical scanner, and generating pulse commands; and
a data acquisition unit receiving the pulse commands, forwarding the pulse commands to the probe, receiving detected signal information from the probe, and forwarding the detected signal information to the controller.

6. The apparatus of claim 1, comprising a calculator of the gain correction map including:
an analog to digital converter to digitize a plurality of signal amplitude values of signals detected by the probe;
a gate to extract peak values from the digitized signal amplitude values, each peak value being obtained within a predetermined time interval;
a detector of a maximum value among the peak values; and
a normalizer to determine each gain value as a ratio of each peak value over the maximum value.

7. The apparatus of claim 6, further comprising an amplifier of the signals detected by the probe, wherein:
the analog to digital converter digitizes the signal amplitude values of the signals detected by the probe and amplified by the amplifier; and
the controller is further configured to apply software amplification to the amplified and digitized signal amplitude values.

8. The apparatus of claim 1, wherein the controller is further configured to interpolate the first gain values of the first gain correction map or to interpolate the second gain values of the second gain correction map if a number of the first or second scanning points on the surface of the reference object is not equal to a number of the third or fourth scanning points on the surface of the test object.

9. The apparatus of claim 1, wherein the controller is further configured to:
filter the first plurality of gain values of the first gain correction map; and
filter the second plurality of gain values of the second gain correction map.

* * * * *